(12) United States Patent
Fujiwara et al.

(10) Patent No.: US 10,830,840 B2
(45) Date of Patent: Nov. 10, 2020

(54) MAGNETIC SENSOR, SENSOR UNIT, MAGNETIC DETECTION DEVICE, AND MAGNETIC MEASUREMENT DEVICE

(71) Applicants: Konica Minolta, Inc., Tokyo (JP); Tohoku University, Miyagi (JP)

(72) Inventors: Kousuke Fujiwara, Miyagi (JP); Mikihiko Oogane, Miyagi (JP); Yasuo Ando, Miyagi (JP); Junichi Jono, Tokyo (JP); Takashi Terauchi, Tokyo (JP)

(73) Assignees: KONICA MINOLTA, INC., Tokyo (JP); TOHOKU UNIVERSITY, Miyagi (JP)

( * ) Notice: Subject to any disclaimer, the term of this patent is extended or adjusted under 35 U.S.C. 154(b) by 97 days.

(21) Appl. No.: 16/065,539

(22) PCT Filed: Dec. 28, 2016

(86) PCT No.: PCT/JP2016/089053
§ 371 (c)(1),
(2) Date: Jun. 22, 2018

(87) PCT Pub. No.: WO2017/115839
PCT Pub. Date: Jul. 6, 2017

(65) Prior Publication Data
US 2019/0018083 A1     Jan. 17, 2019

(30) Foreign Application Priority Data

Dec. 28, 2015 (JP) .............................. 2015-256150

(51) Int. Cl.
*G01R 33/09* (2006.01)
*G01R 33/02* (2006.01)
(Continued)

(52) U.S. Cl.
CPC ........ *G01R 33/098* (2013.01); *A61B 5/04005* (2013.01); *G01R 33/0029* (2013.01);
(Continued)

(58) Field of Classification Search
None
See application file for complete search history.

(56) References Cited

U.S. PATENT DOCUMENTS

2004/0246788 A1  12/2004  Sone et al.
2013/0165766 A1   6/2013  Nishikawa et al.

FOREIGN PATENT DOCUMENTS

EP    1494295 A1   1/2005
EP    2891892 A2   1/2016
(Continued)

OTHER PUBLICATIONS

International Search Report dated Mar. 21, 2017 for PCT/JP2016/089053.
(Continued)

*Primary Examiner* — Paresh Patel
(74) *Attorney, Agent, or Firm* — Lucas & Mercanti, LLP

(57) ABSTRACT

There are provided: an element array 10a including a plurality of tunnel magnetoresistive elements 20 respectively having a fixed magnetic layer 21, a free magnetic layer 22, and an insulation layer 23 provided between the fixed magnetic layer 21 and the free magnetic layer 22, the elements respectively for varying the tunnel resistance of the insulation layer 23 by influence of an external magnetic field; and an electric circuit 30 that applies a voltage to a plurality of the tunnel magnetoresistive elements 20 forming the element array 10a, with the voltage to be applied to each tunnel magnetoresistive element being equal to or higher than 0.1 mV and equal to or lower than 50 mV.

15 Claims, 9 Drawing Sheets

(51) Int. Cl.
H01L 43/08 (2006.01)
G01R 33/10 (2006.01)
A61B 5/04 (2006.01)
G01R 33/00 (2006.01)

(52) U.S. Cl.
CPC ............ *G01R 33/02* (2013.01); *G01R 33/09* (2013.01); *G01R 33/093* (2013.01); *G01R 33/10* (2013.01); *H01L 43/08* (2013.01); *A61B 2562/0223* (2013.01)

(56) References Cited

FOREIGN PATENT DOCUMENTS

| | | | | | |
|---|---|---|---|---|---|
| JP | H11112054 | A | | 4/1999 | |
| JP | 2001093119 | A | | 4/2001 | |
| JP | 2004093576 | A | | 3/2004 | |
| JP | 2008170368 | A | * | 7/2008 | |
| JP | 2008170368 | A | | 7/2008 | |
| JP | 2011102730 | A | | 5/2011 | |
| JP | 2011103336 | A | | 5/2011 | |
| JP | 2012152515 | A | * | 8/2012 | |
| JP | 2012152515 | A | | 8/2012 | |
| JP | 2013175615 | A | | 9/2013 | |
| JP | 2015125019 | A | | 7/2015 | |
| JP | 2017096627 | A | * | 6/2017 | ........... G01R 33/098 |
| WO | 2012014415 | A1 | | 2/2012 | |
| WO | WO-2012014415 | A1 | * | 2/2012 | ............ B82Y 10/00 |
| WO | 2012032962 | A1 | | 3/2012 | |
| WO | 2012161037 | A1 | | 11/2012 | |
| WO | 2015146656 | A1 | | 10/2015 | |

OTHER PUBLICATIONS

Extended European Search Report dated Jan. 4, 2019 from corresponding EP Application No. 16881813.6.
Tondra Mark et al: "Picotesla field sensor design using spin-dependent tunneling devices", Journal of Applied Physics, American Institute of Physics, US, vol. 83, No. 11, Jun. 1, 1998 (Jun. 1, 1998), pp. 6688-6690, XP012044140, ISSN: 0021-8979, DOI: 10.1063/1.367861 * abstract * * Section II Sensor design *.
Chaves R et al: "Low frequency picotesla field detection using hybrid MgO based tunnel sensors", Applied Physics Letters, A I P Publishing LLC, US, vol . 91, No. 10, Sep. 5, 2007 (Sep. 5, 2007), pp. 102504-102504, XP012099044, ISSN: 0003-6951, DOI: 10.1063/1.2775802 * abstract; figures *.
Written Opinion of the International Searching Authority dated Mar. 21, 2017 from corresponding International Application No. PCT/JP2016/089053 and English translation.
CNIPA, Office Action for corresponding Chinese patent application No. 201680076140.4, dated Nov. 25, 2019, with partial English translation.
CNIPA, Office Action dated Jul. 13, 2020, which was issued in connection with corresponding Chinese patent application No. 201680076140.4, with partial English translation. (11 pages).

* cited by examiner

MAGNETIC SENSOR, SENSOR UNIT, MAGNETIC DETECTION DEVICE, AND MAGNETIC MEASUREMENT DEVICE

CROSS REFERENCE TO RELATED APPLICATION

This Application is a 371 of PCT/JP2016/089053 filed on Dec. 28, 2016, which, in turn, claimed the priority of Japanese Patent Application No. 2015-256150 filed on Dec. 28, 2015, both applications are incorporated herein by reference.

TECHNOLOGICAL FIELD

The present invention relates to a magnetic sensor including tunnel magnetoresistive elements, a sensor unit, a magnetic detection device and a magnetic measurement device.

BACKGROUND

Application of tunnel magnetoresistive elements is expected in the field of magnetic sensors, magnetic heads, magnetic memories, or the like. Magnetic detection devices that use tunnel magnetoresistive elements have achieved a high sensitivity by connecting a large number of tunnel magnetoresistive elements in series or in parallel (see Patent Literatures 1 to 4).

For example, a device described in Patent Literature 1 is intended to reduce noise and improve sensitivity of a magnetic sensor implemented by connecting, in parallel or in series, a first cell formed by connecting tunnel magnetoresistive elements in parallel and further connecting the resultant sequences of elements in parallel, and a second cell formed by connecting tunnel magnetoresistive elements in parallel and further connecting the resultant sequences of elements in series.

In a device described in Patent Literature 2, two or more tunnel magnetoresistive elements including pinned layers with mutually different directions of magnetization are formed on a single chip so that magnetic fields with different directions may be detected. Here, the tunnel magnetoresistive elements turn out to be a group of tunnel magnetoresistive elements including a plurality of serially connected tunnel magnetoresistive elements.

In a device described in Patent Literature 3, there is disclosed a biomagnetic measurement system including a large number of integrated bodies respectively including TMR modules having a large number of tunnel magnetoresistive elements arranged in parallel and/or in series, together with a disclosure with regard to bridge-connecting the TMR modules to form a differential amplification circuit.

In a device described in Patent Literature 4, a voltage is applied to a sensor element including a plurality of serially connected ferromagnetic tunnel elements so that the sensor element operates in a highly sensitive state.

Raising the integration degree of tunnel magnetoresistive elements included in a magnetic sensor formed by connecting the tunnel magnetoresistive elements in series or in parallel as described in Patent Literatures 1 to 4 allows for reducing noise of the magnetic sensor. On the other hand, raising the integration degree of the magnetic sensor may result in decreased signal level of the magnetic sensor due to variation among elements or defective elements. Note that, although raising the voltage being supplied to the magnetic sensor increases the sensitivity, there is generally also an increase of noise and, as a result, no more substantial improvement of sensitivity.

CITATION LIST

Patent Literature

Patent Literature 1: Japanese Patent Laid-Open No. 2011-102730
Patent Literature 2: Japanese Patent Laid-Open No. 2004-93576
Patent Literature 3: International Patent Publication No. 2012/161037
Patent Literature 4: Japanese Patent Laid-Open No. 11-112054

SUMMARY

It is an object of the present invention, which has been made in view of the aforementioned Background, to provide a magnetic sensor that reduces noise, while raising the signal level.

In addition, it is also an object of the present invention to provide a sensor unit having the magnetic sensor incorporated therein, a magnetic detection device and a magnetic measurement device.

To achieve the aforementioned objects, the magnetic sensor according to the present invention has an element array including a plurality of tunnel magnetoresistive elements respectively having a fixed magnetic layer, a free magnetic layer, and an insulation layer provided between the fixed magnetic layer and the free magnetic layer, the elements respectively for varying the tunnel resistance of the insulation layer by influence of an external magnetic field, and an electric circuit that applies a voltage to a plurality of the tunnel magnetoresistive elements forming the element array, the voltage to be applied to each tunnel magnetoresistive element being equal to or higher than 0.1 mV and equal to or lower than 50 mV.

The magnetic sensor allows for reducing noise that occurs in each tunnel magnetoresistive element, while substantially improving the sensitivity of each tunnel magnetoresistive element, by setting the voltage to be applied to each tunnel magnetoresistive element to be equal to or lower than 50 mV. On the other hand, setting the voltage to be applied to each tunnel magnetoresistive element to be equal to or higher than 0.1 mV also allows for preventing the number of serial connections, or the number of parallel connections, of tunnel magnetoresistive elements from excessively increasing, thereby raising the reliability such as non-defective rate of tunnel magnetoresistive elements. In other words, setting the voltage to be applied to insulation layer equal to or higher than 0.1 mV eliminates the necessity of excessively increasing the number of serial connections, or the number of parallel connections, of the tunnel magnetoresistive elements, or making the insulation layer excessively thin to secure sensitivity, whereby it becomes easy to exhibit a moderate bias effect in the tunnel magnetoresistive elements.

To achieve the aforementioned objects, the sensor unit according to the present invention has the aforementioned plurality of magnetic sensors integrated therein by coupling via serial connection, parallel connection, or both the serial connection and the parallel connection.

The aforementioned sensor unit turns out to exhibit an effect of improved sensitivity and reduced noise by inclusion of the aforementioned magnetic sensor.

To achieve the aforementioned objects, the magnetic detection device according to the present invention has at least one of the aforementioned magnetic sensors, and a controller that performs signal processing of a detection output from the at least one magnetic sensor.

The aforementioned magnetic detection device turns out to exhibit an effect of improved sensitivity and reduced noise by inclusion of the aforementioned magnetic sensor.

To achieve the aforementioned objects, a magnetic measurement device for a biological body according to the present invention has a biomagnetic field detector having the aforementioned plurality of magnetic sensors and provided under the influence of a magnetic field from a biological body, and a controller that performs signal processing of an output of the biomagnetic field detector.

The aforementioned magnetic measurement device turns out to exhibit an effect of improved biosensitivity and reduced noise by inclusion of the aforementioned magnetic sensor.

DETAILED DESCRIPTION OF EMBODIMENTS

[First Embodiment]

In the following, a magnetic sensor of a first embodiment according to the present invention will be explained, referring to drawings.

Figure 1:
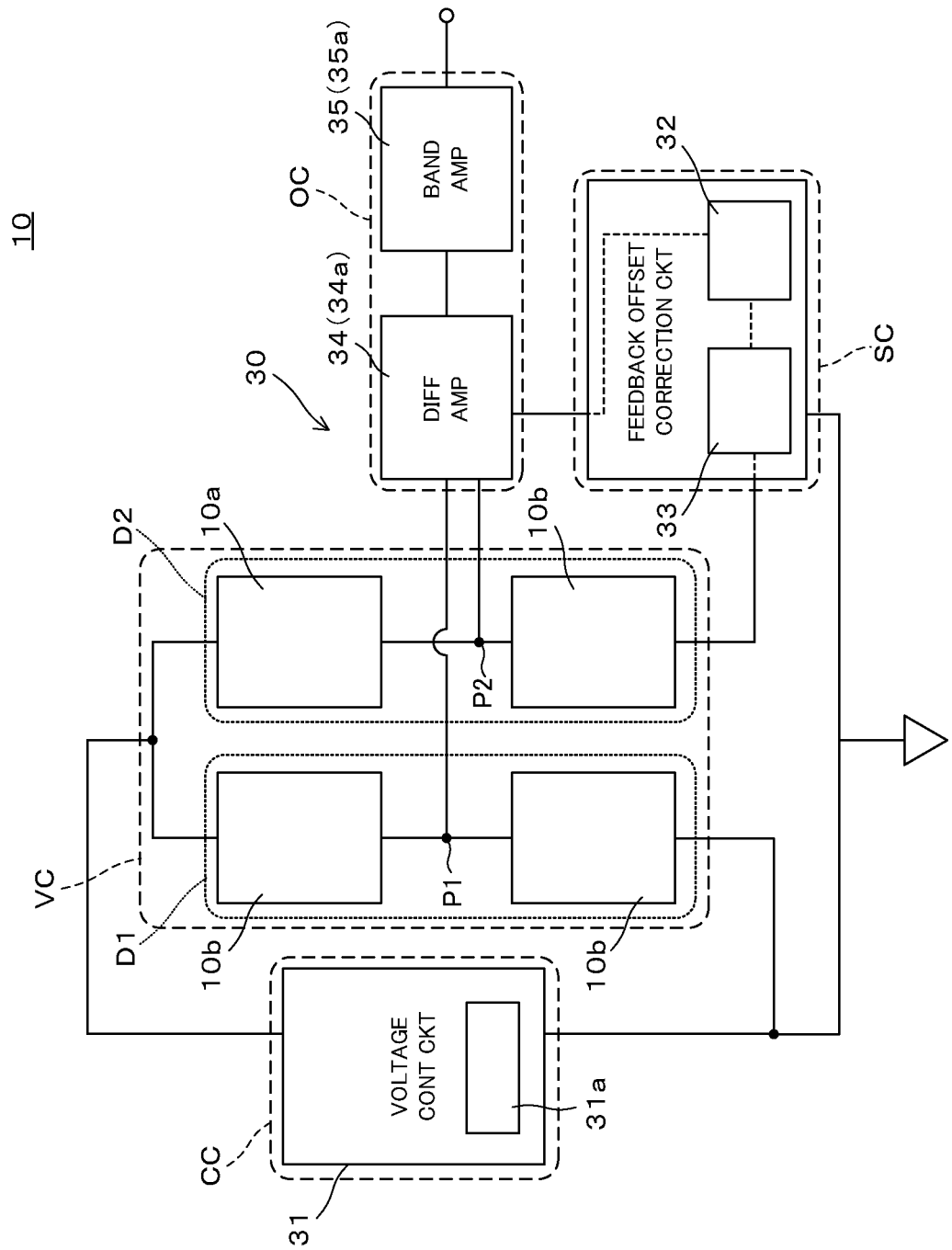
FIG. 1 is a conceptual diagram explaining a magnetic sensor according to a first embodiment.

A magnetic sensor 10 illustrated in FIG. 1 is a hybrid circuit and detects a very weak magnetic field strength such as a biomagnetic field, for example, at room temperature or below. The magnetic sensor 10 includes a bridge circuit VC, a voltage control circuit CC, a correction circuit SC, and an output circuit OC. In the magnetic sensor 10, the voltage control circuit CC, the correction circuit SC, and the output circuit OC are configured as an electric circuit 30 for driving.

The bridge circuit VC is configured as a Wheatstone bridge type circuit, and formed by an element array 10a including a plurality of tunnel magnetoresistive elements (TMR elements) 20, and fixed resistors 10b. The fixed resistor 10b is an element with a fixed resistance value and exhibits little environmental variation such as temperature, or the like. Although the magnetic sensor 10 is formed by one element array 10a and three fixed resistors 10b in the example of FIG. 1, it may be formed by two or more element arrays 10a. Specifically, the magnetic sensor 10 may be formed by two element arrays 10a having for example the bridge circuits VC provided in series, and two fixed resistors 10b arranged in series. Furthermore, the bridge circuit VC may be formed by four element arrays 10a by adjusting the sensitivity direction of the element arrays 10a.

Figure 2:
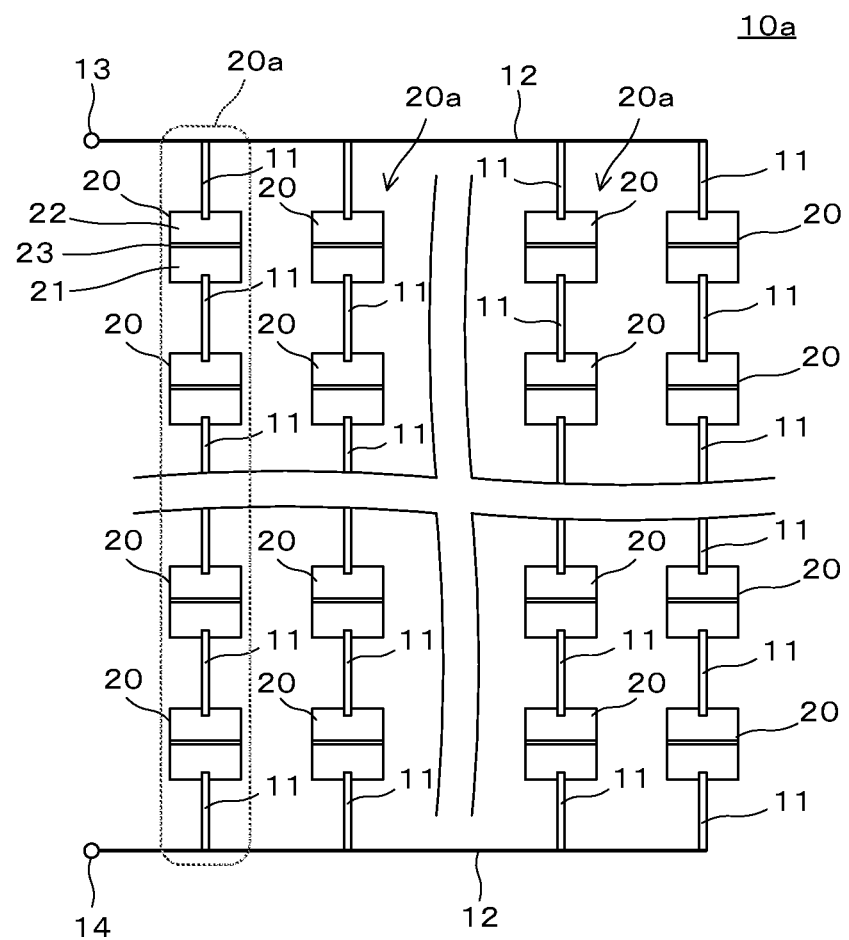
FIG. 2 is a conceptual diagram explaining an element array forming the magnetic sensor of FIG. 1.
Figure 3:
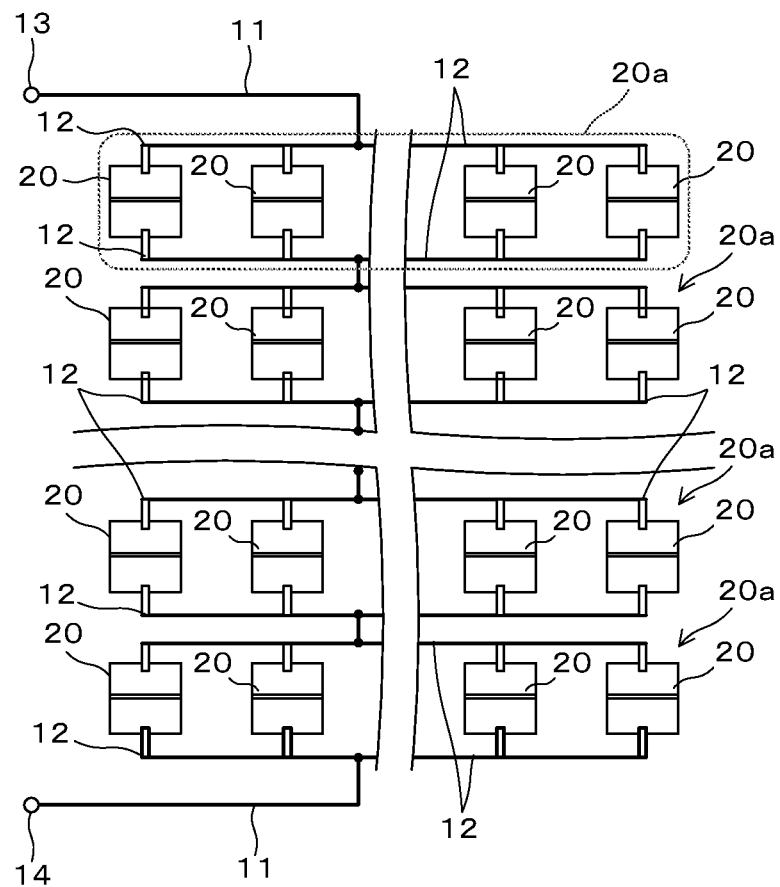
FIG. 3 is an explanatory diagram of a vasriation of the element array illustrated in FIG. 2.

As illustrated in FIG. 2, the element array 10a forming the bridge circuit VC in the magnetic sensor 10 of FIG. 1 is formed by both a serial connection and a parallel connection of a plurality of tunnel magnetoresistive elements 20. Accordingly, it is possible to appropriately combine a plurality of the tunnel magnetoresistive elements 20 so as to improve the sensitivity and reduce the noise of the magnetic sensor 10. The adjacent tunnel magnetoresistive elements 20 are aligned in a same direction and connected in series by a wiring 11 into a magnetoresistive element group 20a. There are a plurality of serially connected magnetoresistive element groups 20a, which are placed on two-dimensional grid points, for example, and connected in parallel by a wiring 12. The element array 10a includes 20 or more and 10,000 or less of the tunnel magnetoresistive elements 20 connected in series. Providing 20 or more the tunnel magnetoresistive elements 20 realizes effective improvement of sensitivity and reduction of noise with regard to detection of a very weak magnetic field. In addition, providing 10,000 or less the tunnel magnetoresistive elements 20 allows for reducing the cost while avoiding upsizing. Note that, as illustrated in FIG. 3, the element arrays 10a may be formed by forming the magnetoresistive element group 20a by connecting the tunnel magnetoresistive elements 20 in parallel, and connecting a plurality of the parallel-connected magnetoresistive element groups 20a in series.

Figure 4A:
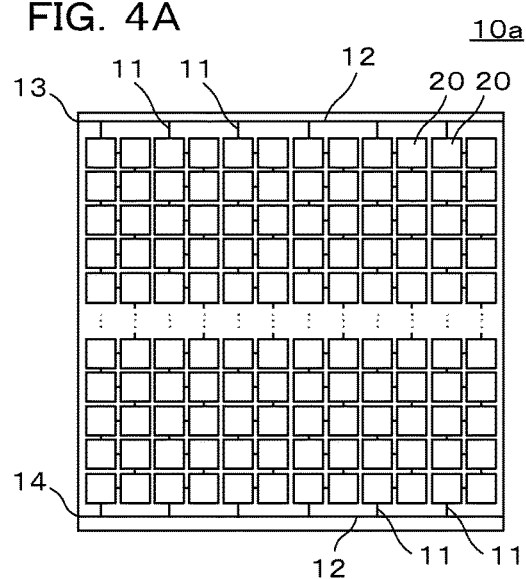
FIGS. 4A to 4E are a conceptual diagrams describing a spatial arrangement of magnetoresistive elements in an element array.
Figure 4B:
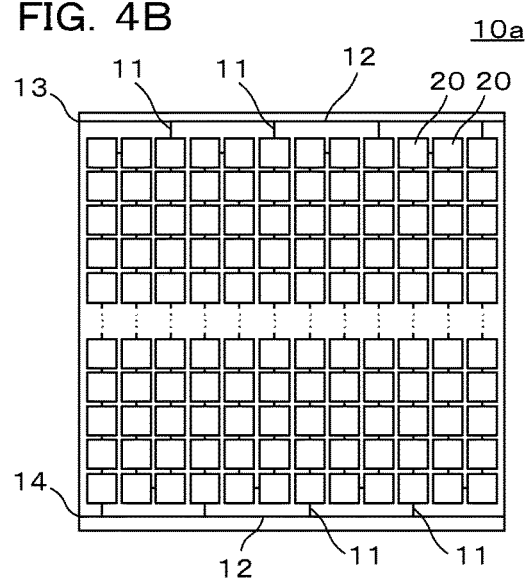
Figure 4C:
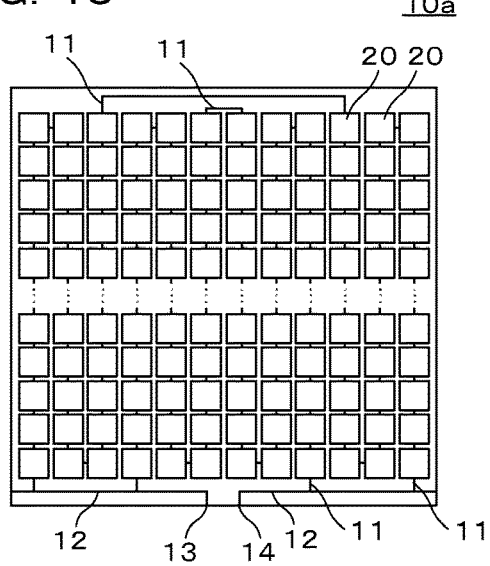

When setting the number of serial connections or the number of parallel connections of the tunnel magnetoresistive elements 20 so as to have a required resistance value, on the basis of the spatial arrangement of FIGS. 2 and 3, the wiring 11 may also be provided in a zig-zag manner, as illustrated for example in FIGS. 4A and 4B described below. Accordingly, the flexibility within an acceptable space of the element array 10a rises. In addition, as illustrated in FIG. 4C, the tunnel magnetoresistive elements 20 may also be connected in series and in parallel by an arrangement in which electrodes 13 and 14 are shifted to one side.

Figure 4D:
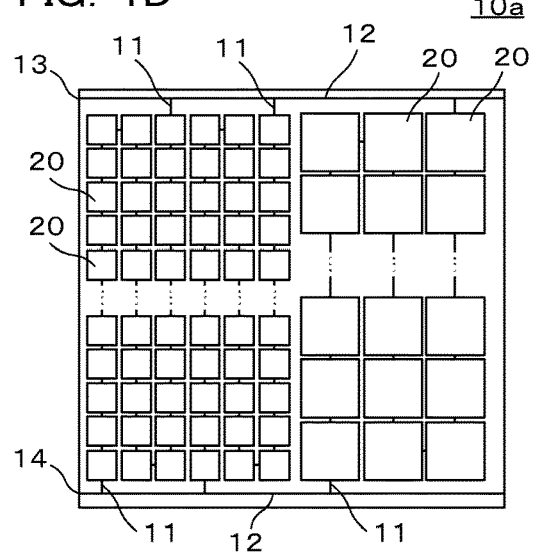

When only one of the magnetoresistive element groups 20a has an extremely low resistance value, electric current concentrates there, preventing the element array 10a as a whole from exhibiting its performance efficiently. Therefore, it is important not to cause a difference of resistance values between respective magnetoresistive element groups 20a when the tunnel magnetoresistive elements 20 are connected in series. However, variation of the film thickness of an insulation layer 23 also causes variation of resistance values of respective tunnel magnetoresistive elements 20. Accordingly, as illustrated in FIG. 4D, there may be a configuration in which the area of the tunnel magnetoresistive elements 20 is increased in a region where the film thickness of the insulation layer 23 thickens so as to reduce the resistance value, and adjust the substantial impedances between respective magnetoresistive element groups 20a. The impedance matching described above may be performed not only by adjusting the area of the tunnel magnetoresistive elements 20 but also by changing the number of respective parallel connections on the basis of the arrangement of FIG. 3.

Figure 4E:
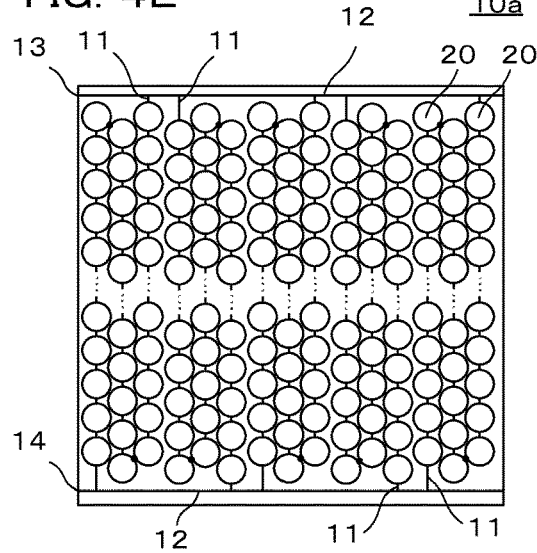

Note that, the shape of the tunnel magnetoresistive elements 20 is not limited to rectangular, and the element array 10a may be formed by combining the circular tunnel magnetoresistive elements 20 as illustrated in FIG. 4E, for example.

Although the foregoing explanation is an example when regarding the spatial arrangement of the tunnel magnetoresistive elements 20 as a plane, there may be a configuration that secures the number of arrays in the height direction by laminating a number of layers of silicon wafers having films, for example.

The element array 10a is connected to the high electric potential side of a voltage control circuit 31 illustrated in FIG. 1 via one electrode 13, and connected to the output circuit OC at the detecting side via the other electrode 14. The resistance value of the tunnel magnetoresistive elements 20 varies due to the influence of a magnetic field. Accordingly, the electric potential of the electrode 14 of the element array 10a varies and, as a result, the output of the magnetic sensor 10 as a whole also varies. Detection of the electric potential variation of the element array 10a allows for detecting the magnetic field, although details of which will be explained below. Furthermore, a number of magnetoresistive element groups 20a allow for securing electric current, whereby the detection output of the magnetic sensor 10 may be stabilized.

The resistance value of the element array 10a is equal to or higher than 0.1 kΩ and equal to or lower than 10 kΩ. The voltage applied to the element array 10a is equal to or higher than 0.1 V and equal to or lower than 20 V. The aforementioned ranges of the resistance value and the voltage may be supported by a relatively general sensor circuit, for which general amplification circuits, voltage sources, or the like, may be used as components of the electric circuit 30 of the magnetic sensor 10, whereby highly-precise signal detection using a simple circuit becomes easy.

Figure 5A:
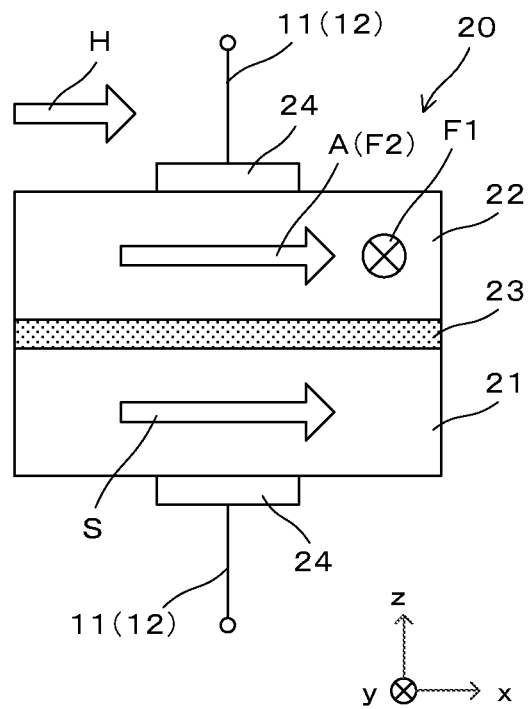
FIGS. 5A and 5B are enlarged views describing tunnel magnetoresistive elements forming the magnetic sensor.
Figure 5B:
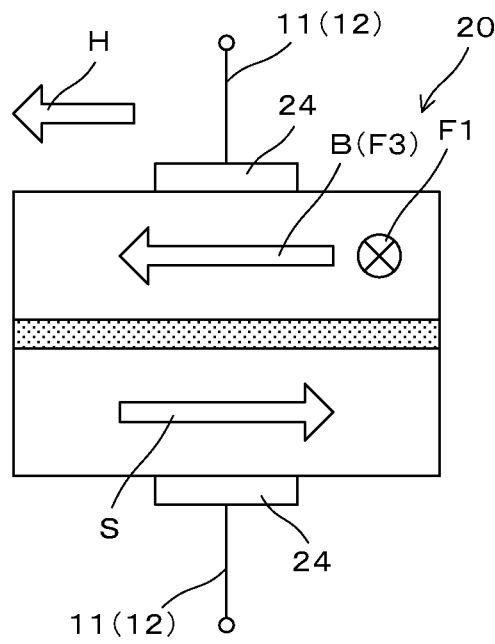

As illustrated in an enlarged manner in FIGS. 5A and 5B, each of the tunnel magnetoresistive elements 20 has a fixed magnetic layer 21, a free magnetic layer 22, and the insulation layer 23 provided between the fixed magnetic layer 21 and the free magnetic layer 22. Electrodes 24 are provided at both ends of the tunnel magnetoresistive element 20, the electrode 24 being connected to the wiring 11 (or the wiring 12).

The fixed magnetic layer 21 has a fixed magnetization direction, whereas the magnetization direction of the free magnetic layer 22 varies due to being influenced by a magnetic flux from the outside. The insulation layer 23 changes the tunnel current flowing from the fixed magnetic layer 21 to the free magnetic layer 22 in accordance with an angle difference between the magnetization direction of the fixed magnetic layer 21 and the magnetization direction of the free magnetic layer 22. In other words, the resistance value of the tunnel magnetoresistive element 20 varies in accordance with the variation of the magnetic flux passing through the tunnel magnetoresistive element 20.

In the same element array 10a, a plurality of the tunnel magnetoresistive elements 20 are aligned in the same direction, with the magnetization directions of the fixed magnetic layers 21 of a plurality of the tunnel magnetoresistive elements 20 being substantially matching. Note that, although it is ideal, in the element array 10a, that the magnetization directions of the fixed magnetic layers 21 of all the tunnel magnetoresistive elements 20 match each other, it suffices that the magnetization directions match within a range that does not hinder biomagnetic measurement.

In addition, as a result that a plurality of the tunnel magnetoresistive elements 20 forming the same element array 10a are aligned in the same direction, the magnetization directions of the free magnetic layers 22 substantially match each other in a state unaffected by the magnetic field of a plurality of the tunnel magnetoresistive elements 20. With regard to the magnetization directions of the free magnetic layers 22, it suffices that the magnetization directions are aligned within a range that does not hinder biomagnetic measurement, similarly to the case of the fixed magnetic layer 21.

In the following, an example of the magnetization direction and characteristic change of the tunnel magnetoresistive elements 20 will be explained. The magnetization direction S of the fixed magnetic layer 21 of the tunnel magnetoresistive elements 20 illustrated in FIGS. 5A and 5B is parallel with the +x direction. The magnetization direction F1 of the free magnetic layer 22 of the tunnel magnetoresistive elements 20 in a state unaffected by the magnetic field is parallel with a direction which is different from the magnetization direction S of the fixed magnetic layer 21, specifically the +y direction perpendicular thereto.

When a large magnetic field H is applied to the tunnel magnetoresistive elements 20 due to an external magnetic field, the free magnetic layer 22 is magnetized along a particular direction. When the magnetic field H is applied in the same direction as the fixed magnetic layer 21 as illustrated in FIG. 5A, a magnetization direction F2 of the free magnetic layer 22 of the tunnel magnetoresistive elements 20 swings toward the direction of arrow A, which is the same direction as that of the fixed magnetic layer 21. When, on the other hand, the magnetic field H appears in a direction opposite to that of the fixed magnetic layer 21 as illustrated in FIG. 5B, the magnetization direction F3 of the free magnetic layer 22 of the tunnel magnetoresistive elements 20 swings toward the direction of arrow B, which is a direction opposite to that of the fixed magnetic layer 21.

Here, in the tunnel magnetoresistive elements 20, the swing of the magnetization direction of the free magnetic layer 22 toward the same direction as the magnetization direction of the fixed magnetic layer 21 causes the tunnel currents to increase and the resistance value of the insulation layer 23 to decrease, and the swing toward the opposite direction causes the tunnel currents to decrease and the resistance value of the insulation layer 23 to increase. Therefore, the resistance value of the tunnel magnetoresistive elements 20 illustrated in FIG. 5A decreases, and the resistance value of the tunnel magnetoresistive elements 20 illustrated in FIG. 5B increases. The resistance value of the tunnel magnetoresistive elements 20 varies within a predetermined range in accordance with the strength of the magnetic field H. Accordingly, the resistance varies in the element array 10a as a whole having the tunnel magnetoresistive elements 20 integrated in series, and the electric potential between the electrodes 13 and 14 of the element array 10a varies. The electric potential between the electrodes 13 and 14 of the element array 10a is detected as a potential difference in the bridge circuit VC of FIG. 1, the output (specifically, output voltage) of the magnetic sensor 10 varies, and a magnetic detection signal is obtained.

The fixed magnetic layer 21 is made from, for example, CoFeB, CoFe, or the like. In addition, the free magnetic layer 22 is made from, for example, NiFe, CoFe, CoNiFe, CoZrNb, or the like.

The voltage applied to each of the tunnel magnetoresistive elements 20 (substantially, the voltage applied to the insulation layer 23) is equal to or higher than 0.1 mV and equal to or lower than 50 mV. The tunnel magnetoresistive elements 20 respectively cause the tunnel resistance of the insulation layer 23 to vary by to the effect of an external magnetic field, as had been explained.

Setting the voltage applied to each of the tunnel magnetoresistive elements 20 (substantially, the voltage applied to the insulation layer 23) equal to or lower than 50 mV allows for reducing the noise that may occur in each of the tunnel magnetoresistive elements 20, while substantially improving the sensitivity of each of the tunnel magnetoresistive elements 20. On the other hand, setting the voltage applied to the insulation layer 23 of each of the tunnel magnetoresistive elements 20 equal to or higher than 0.1 mV allows for preventing the number of serial connections or the number of parallel connections of the tunnel magnetoresistive elements 20 from excessively increasing, which may also lead to raising the reliability of the tunnel magnetoresistive elements 20 such as the non-defective rate. In other words, setting the voltage applied to the insulation layer 23 equal to or higher than 0.1 mV eliminates the necessity of excessively increasing the number of serial connections or the number of parallel connections of the tunnel magnetoresistive elements 20, or making the insulation layer 23 excessively thin, whereby it becomes easy to cause the tunnel magnetoresistive elements 20 to exhibit a moderate bias effect.

Figure 6:
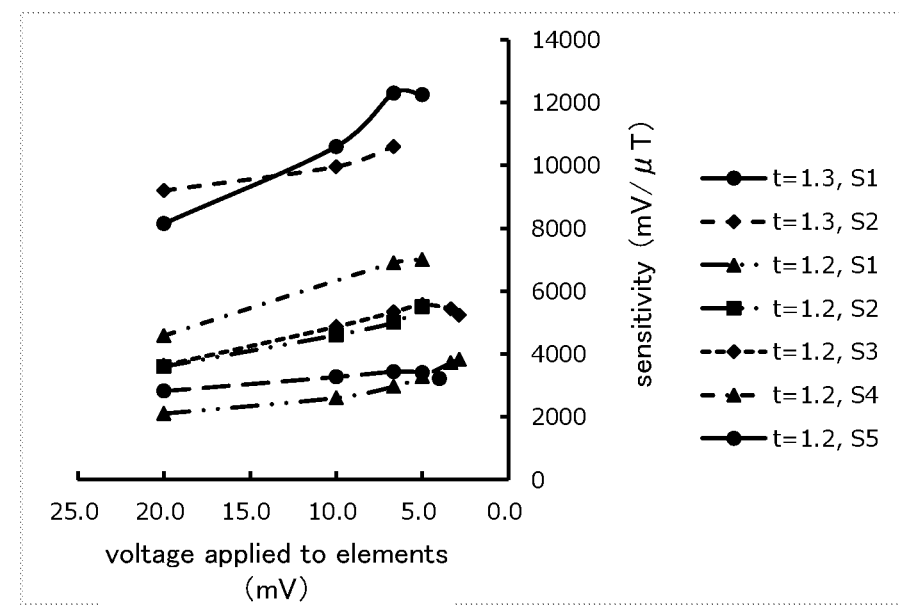
FIG. 6 is an explanatory diagram of the relation between the voltage applied to tunnel magnetoresistive elements and the sensitivity.

FIG. 6 is a chart illustrating the relation between the voltage applied to the tunnel magnetoresistive elements 20 and the sensitivity. The horizontal axis indicates the voltage applied to the tunnel magnetoresistive elements 20 or a bias voltage (mV), and the vertical axis indicates the ratio between the detected potential difference (mV) and the strength (µT) of the external magnetic field. The detected potential difference (mV) is a potential difference observed via an amplifier having an appropriate amplification factor, the potential difference occurring on the bridge circuit due to variation of the resistance value of the tunnel magnetoresistive elements 20 being affected by an external magnetic field. The amplification factor of the amplifier is set in accordance with the performance of the tunnel magnetoresistive elements 20 and the magnetic field strength to be detected, so that an easy-to-handle output (for example, output from about a few 100 mV to 1 V) is obtained. In the illustrated chart, samples with different numbers of serial connections of the tunnel magnetoresistive elements 20 have been plotted. In the case of the example illustrated in FIG. 6, the lower the voltage applied to the insulation layer 23 is, the more the performance of sensitivity improves. For this, even a small voltage (about several tens of 10 mV) may be considered to cause a bias effect since the insulation layer 23, which is a barrier layer, is thin. Therefore, it is further desirable that the voltage applied to the tunnel magnetoresistive elements 20 (substantially, the voltage applied to the insulation layer 23) is equal to or higher than 0.5 mV and equal to or lower than 20 mV. In such a case, sensitivity improvement and noise reduction of the tunnel magnetoresistive elements 20 is further ensured, and it is also possible to produce the highly reliable tunnel magnetoresistive elements 20 relatively easy.

In the tunnel magnetoresistive elements 20, the resistance value per unit area of the insulation layer 23 is equal to or higher than $1 \times 10^3 \Omega/\mu m^2$ and equal to or lower than $1 \times 10^{12} \Omega/\mu m^2$. Setting the resistance value equal to or higher than the lower limit $1 \times 10^3 \Omega/\mu m^2$ allows for securing the film thickness to some extent and suppressing occurrence of a short circuit, and setting the resistance value equal to or lower than the upper limit $1 \times 10^{12} \Omega/\mu m^2$ allows for securing occurrence of tunnel current and preventing decrease of the sensitivity of the tunnel magnetoresistive elements 20. Note that, when the resistance value is within the aforementioned range, film thickness of the insulation layer 23 turns out to be about 1.0 to 3.0 nm, for example. In the case where the film thickness is such a degree, the TMR ratio may be increased as the film thickness increases. The TMR ratio is defined by $(R2-R1)/R1 \times 100$ (%). Here, the value R1 is the resistance value in the case where the magnetization direction of the fixed magnetic layer 21 and the magnetization direction of the free magnetic layer 22 are same directions (referred to a parallel state), and the value R2 is the resistance value in the case where the magnetization direction of the fixed magnetic layer 21 and the magnetization direction of the free magnetic layer 22 are opposite directions (referred to as anti-parallel state).

Figure 7:
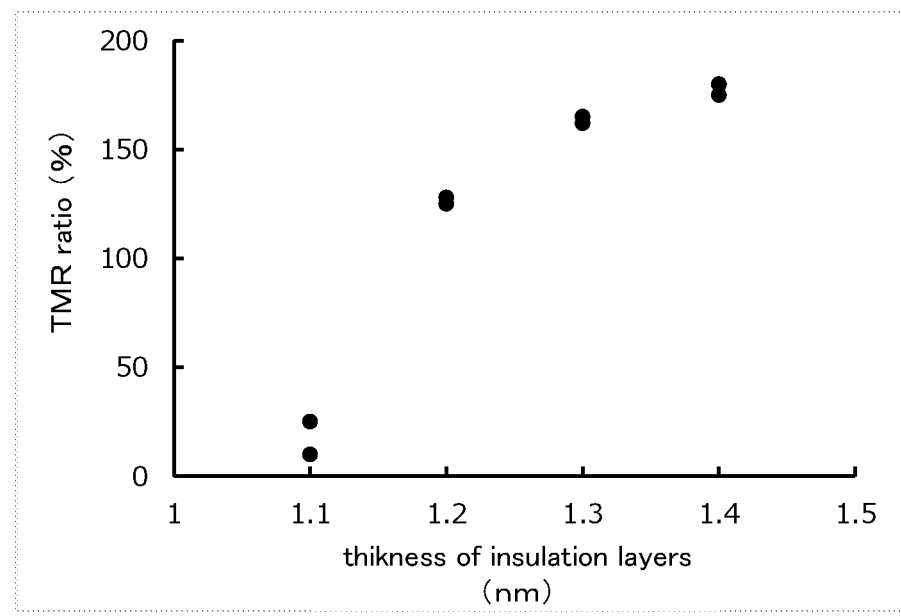
FIG. 7 is an explanatory diagram of the relation between the insulation layer film thickness and the TMR ratio of tunnel magnetoresistive elements.

FIG. 7 is an explanatory diagram of the relation between the film thickness of the insulation layer 23 and the TMR ratio in the case where the insulation layer 23 is made from magnesium oxide (MgO). As illustrated in the diagram, it can be seen from the result of TMR ratio measurement in the sample with the film thickness of the insulation layer 23 being 1.1 to 1.4 nm that the higher the sensitivity, the thicker the film thickness is. Particularly, the TMR ratio exhibits almost the highest performance with the film thickness being 1.4 nm. From the result, it is preferable for the film thickness of the insulation layer 23 to be equal to or higher than 1.1 nm and equal to or lower than 3.0 nm, and further preferable to be, equal to or higher than 1.2 nm and equal to or lower than 2.5 mm Therefore, it may be further preferable for the resistance value per unit area of the insulation layer 23 made from MgO to be equal to or higher than $2 \times 10^3 \Omega/\mu m^2$ and equal to or lower than $2 \times 10^9 \Omega/\mu m^2$.

The area of the insulation layer 23 is equal to or larger than 1 µm² and equal to or smaller than 1 mm². The area of the insulation layer 23 is an area in a direction perpendicular to the film thickness direction of the insulation layer 23. Setting the area of the insulation layer 23 equal to or larger than the lower limit 1 µm² allows for improving the manufacturing precision and processibility of the tunnel magnetoresistive elements 20 including the insulation layer 23, and setting the area of the insulation layer 23 equal to or smaller than the upper limit 1 mm² allows for suppressing occurrence of initial failure due to dust or the like during manufacturing and increasing the reliability of the tunnel magnetoresistive elements 20.

It is further preferable for the area of the insulation layer 23 to be equal to or larger than 25 µm² and equal to or smaller than 0.04 mm².

The insulation layer 23 is made from a material with a coherent tunneling effect. The coherent tunneling effect allows for increasing the TMR ratio and improving the sensitivity of the tunnel magnetoresistive elements 20, and the element array 10*a* as well. The insulation layer 23 is specifically made from one of: magnesium oxide, spinel, or aluminum oxide.

In the following, the noise reduction effect resulting from integration of the tunnel magnetoresistive elements 20 will be explained.

For example, increasing the number of serial connections of the tunnel magnetoresistive elements 20, while keeping the bridge voltage applied to the bridge circuit VC or the applied voltage to the magnetic sensor 10 constant, results in the decrease of the voltage applied to one of the tunnel magnetoresistive elements 20 in accordance with the number of serial connections. The size $S_v$ of the 1/f noise of the tunnel magnetoresistive element 20 is given by the following typical formula (1);

$$S_v = \frac{\alpha V^2}{Af}(V^2/Hz) \qquad (1)$$

where, in the above formula (1), $\alpha$ is a coefficient, V is the voltage (element voltage) of one of the tunnel magnetoresistive elements 20, A is the element area, and f is the frequency. In other words, when only the element voltage V is a variable, the voltage component of the noise that occurs in one of the tunnel magnetoresistive elements 20 is regarded to be proportional to the square root of size $S_v$ of the aforementioned noise, i.e., the element voltage V.

Assuming that the total amount of noise of all the tunnel magnetoresistive elements 20 connected in series, i.e., the voltage noise strength $S_{noise}$ of the noise in the output of the magnetic sensor 10 is given by the square root of sum of squares of the voltage components of noise that occurs in each of the tunnel magnetoresistive elements 20, the following formula (2) or (3) is expected to hold with regard to the voltage noise strength $S_{noise}$ indicating the total amount of noise, with the number of the serially connected elements being denoted by N and the other components being collectively represented by the coefficient C or C'. Note that, in formula (3), N×V, i.e., the applied voltage to the magnetic sensor 10 is assumed to be constant. This means that increasing the number of the serially connected elements while keeping the applied voltage constant reduces noise by a factor of 1/√N.

$$S_{noise} = C \times \sqrt{N} \times V (V/\sqrt{Hz}) \qquad (2)$$

$$S_{noise} = C' \times \sqrt{1/N}(V/\sqrt{Hz}) \qquad (3)$$

In addition, it is expected, from the aforementioned typical formula (1) expressing the size $S_v$ of the 1/f noise that occurs in the tunnel magnetoresistive elements 20, that the following typical formula (4) holds, using another coefficient C'', with regard to the influence on the voltage noise strength $S_{noise}$ due to increase of the element area A.

$$S_{noise} = C'' \times \sqrt{1/A} \times (V/\sqrt{Hz}) \qquad (4)$$

In other words, the same effect as the noise reduction resulting from serial connection may also be expected for the noise reduction effect resulting from the effective increase of the element area A by increasing the number of parallel connections of the tunnel magnetoresistive elements 20 while keeping the bridge voltage constant. From the foregoing description, the larger the number of serial and parallel connections, the more improvement of noise reduction effect may be expected (distribution of element voltage and expansion of element area), and therefore it is desirable to provide as large a number of connections as possible within a range that allows processing. Note that, although detailed explanation is omitted, a noise reduction effect close to the aforementioned calculation or evaluation has also been confirmed by experiment.

Returning to FIG. 1, the electric circuit 30 configured to drive the bridge circuit VC has the voltage control circuit CC, the correction circuit SC, and the output circuit OC as has already been explained. A voltage is applied to the bridge circuit VC by connecting the voltage control circuit CC and the correction circuit SC of the electric circuit 30. In other words, the electric circuit 30 applies the voltage to the element array 10a (and a plurality of the tunnel magnetoresistive elements 20 as well) and the fixed resistor 10b forming the bridge circuit VC. Specifically, the voltage control circuit CC included in the electric circuit 30 has a power source 31a, and applies a reference voltage to one end of a pair of serial connections D1 and D2 forming the bridge circuit VC including one or more of the element arrays 10a. In addition, the correction circuit SC has a feedback block 32 and a corrector 33, and applies an offset voltage to the other end of the serial connection D2 which is one of the pair of connections forming the bridge circuit VC. In other words, only the reference voltage output from the voltage control circuit CC is applied to the serial connection D1 which is one of the bridge circuit VC, and the reference voltage output from the voltage control circuit CC and a correction voltage output from the correction circuit SC are applied to the other serial connection D2 of the bridge circuit VC.

The correction circuit SC operates to cancel a potential difference between detection terminals P1 and P2 of the bridge circuit VC, by applying a voltage signal, i.e. an offset voltage, obtained from the potential difference between the detection terminals P1 and P2 of the bridge circuit VC to one end of the serial connection D2.

In the correction circuit SC, a differential amplification signal from an amplification block 34 of the output circuit OC described below is input to the feedback block 32. The feedback block 32, including a low-pass filter or the like in practice, feeds back, to the corrector 33, a voltage signal including low-frequency components with high-frequency components having been excluded from the differential amplification signal corresponding to the potential difference between the detection terminals P1 and P2. The corrector 33 applies, to the grounded side (i.e., the fixed resistor 10b) of the serial connection D2 of the bridge circuit VC, a voltage signal, i.e. an offset voltage, that cancels the potential difference between the detection terminals P1 and P2, on the basis of the voltage signal input from the feedback block 32. As a result, control is performed so that the voltage difference between the detection terminals P1 and P2 of the bridge circuit VC becomes equal to or lower than a certain reference value (e.g., 0 V) with regard to the direct current components or ultra-low-frequency components. The aforementioned operation of the correction circuit SC allows for cancelling the voltage difference of direct current or ultra-low-frequency waves that occurs due to a resistance value difference that exhibits even a slight mismatch in the bridge circuit VC, and therefore setting a high amplification factor in the amplification block 34 to detect very small variations of the magnetic field strength. In addition, for example, it is possible to cancel the potential difference, which occurs due to environmental temperature or environmental disturbance, between the bridge circuits VC that vary irrelevantly with the magnetic field desired to be detected. Furthermore, even when the resistance value of the element array 10a does not conform to the design (including the case where some of the tunnel magnetoresistive elements 20 are experiencing a short-circuit), it is possible to provide a simple adjustment so that the average value of the voltage difference between the detection terminals P1 and P2 of the bridge circuit VC turns out to be a desired value (e.g., 0 V).

The output circuit OC has the amplification block 34 and a filter block 35. The amplification block 34 amplifies the output signal, i.e., the potential difference between the detection terminals P1 and P2 of the bridge circuit VC. As the amplification block 34, a difference amplifier 34a including, for example, an operational amplifier or the like is used. In other words, the voltage difference between the detection terminals P1 and P2 of the bridge circuit VC is taken out as an analog voltage amplification signal via the difference amplifier 34a.

The filter block 35 has one of: a low-pass filter, a high-pass filter, or both a low-pass filter and a high-pass filter that selectively allow passing of only components corresponding to magnetic signals in a predetermined band among the amplification signals from the amplification block 34. Although an active type bandpass amplifier 35a, for example, is used as the filter block 35, a passive type band filter may also be used. Voltage amplification signals from the differential amplifier 34a are input to the filter block 35, and after having removed signals in unnecessary frequency bands, only signal values of a voltage focused on a frequency band corresponding to the magnetic field desired to be detected are output.

In the foregoing description, it is necessary to raise the signal strength output from the magnetic sensor 10 and reduce noise to enhance the sensitivity of the magnetic sensor 10.

Generally, to enhance the signal strength, measures may be taken such as providing the magnetic sensor with a structure that exhibits a high tunnel magnetoresistive effect, raising the voltage applied to the magnetic sensor, or the like. Additionally, to reduce noise, measures may be taken such as integrating the tunnel magnetoresistive elements in the magnetic sensor, lowering the voltage applied to the magnetic sensor, or the like. However, integrating the tunnel magnetoresistive elements tends to degrade the tunnel magnetoresistive effect as a magnetic sensor due to performance variation among the elements or interfusion of defective elements. In addition, the voltage applied to the magnetic sensor causes a trade-off between performance of sensitivity and performance of noise, thereby making it difficult to provide the magnetic sensor with an optimal configuration.

Therefore, the present embodiment allows the magnetic sensor 10 to have a structure that secures a high sensitivity performance, and a superior magnetic resolution, while significantly reducing noise, by providing the magnetic sensor 10 with a configuration having integrated a plurality of the tunnel magnetoresistive elements 20 and setting the voltage applied to each of the tunnel magnetoresistive elements 20 equal to or higher than 1.0 mV and is equal to or lower than 50 mV.

In the following, specific examples of the magnetic sensor 10 will be explained.

EXAMPLE 1

In the following, design values of the magnetic sensor 10 of example 1 are listed. The magnetic sensor 10 of example 1 is a high-magnetic-resolution type sensor. The magnetic sensor 10 of example 1 exhibits a relatively large noise reduction effect.
magnetic sensor resistance value: 1.04 kΩ
magnetic sensor area (approximation): 49.73 mm$^2$
magnetic sensor width (as a square): 7.05 mm
bridge circuit voltage (voltage applied to magnetic sensor): 8 V
number of TMR element serial connections: 1110
number of TMR element parallel connections: 5 columns
insulation layer film thickness: 1.35 nm
resistance value per unit area of insulation layer: 3×10$^4$Ω/μm$^2$
TMR element dimension (vertical): 80 μm
TMR element dimension (lateral): 80 μm
area of TMR element (area of insulation layer): 6400 μm$^2$
resistance of TMR element: 4.69 Ω
voltage applied to TMR element: 3.6 mV

EXAMPLE 2

In the following, design values of the magnetic sensor 10 of example 2 are listed. The magnetic sensor 10 of example 2 is a high-spatial-resolution type sensor. The magnetic sensor 10 of example 2 has the tunnel magnetoresistive elements 20 arranged with a high density, and has a relatively small size.
magnetic sensor resistance value: 1.42 kΩ
magnetic sensor area: (approximation) 2.28 mm$^2$
magnetic sensor width: (as a square) 1.51 mm
bridge circuit voltage (voltage applied to magnetic sensor): 8 V
number of TMR element serial connections: 340
number of TMR element parallel connections: 12 columns
insulation layer film thickness: 1.2 nm
resistance value per unit area of insulation layer: 2×10$^4$Ω/μm$^2$
TMR element dimension (vertical): 20 μm
TMR element dimension (lateral): 20 μm
area of TMR element (area of insulation layer): 400 μm$^2$
resistance of TMR element: 50.00 Ω
voltage applied to TMR element: 11.8 mV

EXAMPLE 3

In the following, design values of the magnetic sensor 10 of example 3 are listed. The magnetic sensor 10 of example 3 turns out to exhibit the effect of the present embodiment even in the case where the film thickness of the insulation layer 23 is relatively thick.
magnetic sensor resistance value: 1.11 kΩ
magnetic sensor area (approximation): 3.94 mm$^2$
magnetic sensor width (as a square): 1.98 mm
bridge circuit voltage: 0.5 V
number of TMR element serial connections: 25
number of TMR element parallel connections: 5 columns
insulation layer film thickness: 2.2 nm
resistance value per unit area of insulation layer: 5×10$^6$Ω/μm$^2$
TMR element dimension (vertical): 150 μm
TMR element dimension (lateral): 150 μm
area of TMR element (area of insulation layer): 22500 μm$^2$
resistance of TMR elements: 222.22 Ω
voltage applied to TMR element: 10.0 mV

[Second Embodiment]

In the following, a sensor unit and a magnetic detection device according to a second embodiment will be explained. Note that the magnetic sensors included in the sensor unit or the like of the second embodiment are applications of the magnetic sensor of the first embodiment, and items which are not explained in particular are similar to those of the first embodiment.

Figure 8:
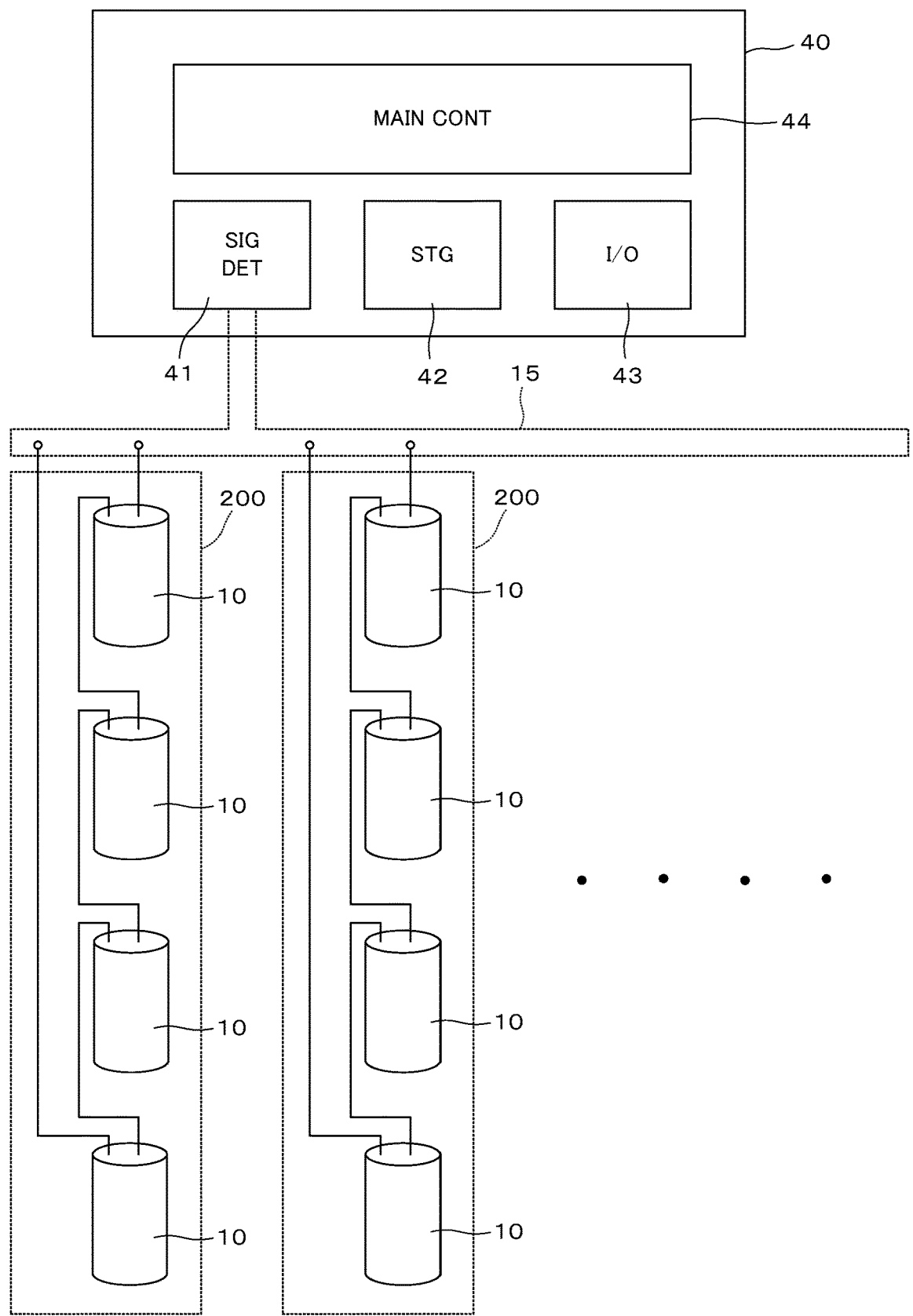
FIG. 8 is a conceptual diagram explaining a sensor unit and a magnetic detection device according to a second embodiment.

As illustrated in FIG. 8, a magnetic detection device 300 has at least one sensor unit 200, and a controller 40. The sensor unit 200 is connected to a controller 40 via a wiring block 15.

The sensor unit 200 is integrated by coupling a plurality of the aforementioned magnetic sensors 10 (see FIG. 1) by serial connection. In FIG. 8, for simplicity, one of the magnetic sensors 10 is illustrated in a cylindrical shape. In the example of FIG. 8, the magnetic detection device 300 has four magnetic sensors 10 arranged on a straight line and connected in series to form a single sensor unit 200, and a plurality of sensor units 200 are arranged in parallel in an adjoining manner. Note that, in the sensor units 200, the magnetic sensors 10 may be coupled by only parallel connection, or by both serial connection and parallel connection.

The controller 40 has a signal detector 41, a storage 42, an input/output block 43, and a main controller 44.

The signal detector 41 of the controller 40 receives detection signals output from each of the sensor units 200 under control of the main controller 44. In the signal detector 41, for example magnetic signals in a predetermined band input and detected from each of the sensor units 200 are converted into an easy-to-process form. Specifically, magnetic signals from the sensor units 200, which are analog signals, are converted into digital signals in the signal detector 41 to be processed in the main controller 44.

The storage 42 stores predetermined programs and data to operate the main controller 44. In addition, the storage 42 stores magnetic signals digitally-converted in the signal detector 41 under control of the main controller 44. The magnetic signals obtained from each of the sensor units 200 may be stored as detection data in association with individual sensor units 200, and such time-series detection data are sequentially recorded in chronological order. Accordingly, the storage 42 may store the result of mapping or the like which has been performed on the measured magnetic signals, in accordance with an instruction from the main controller 44 operating on the basis of a program or an instruction by an operator via the input/output block 43.

The input/output block 43 causes the main controller 44 to start an operation in accordance with a predetermined program by an instruction from an operator, or causes, via an operation of the main controller 44, the signal detector 41 to read, and also store in the storage 42, the detection result of the sensor unit 200. The input/output block 43 operates under control of the main controller 44, and displays the magnetic measurement result obtained from the detection result of the sensor unit 200 on a display or the like, for example.

The main controller 44 integrally controls operation of the signal detector 41, the storage 42, and the input/output block 43. The main controller 44 is capable of performing processes such as filtering, emphasizing, or the like on the magnetic signals obtained via the signal detector 41. In addition, the main controller 44 is capable of compiling the magnetic signals obtained via the signal detector 41. Specifically, the main controller 44 is capable of two-dimensionally mapping the magnetic signal data obtained from each of the sensor units 200, converting the time-series variation into a video image, and causing the input/output block 43 to display the result.

The sensor units 200 and the magnetic detection device 300 explained above turn out to exhibit an effect of improved sensitivity and reduced noise by inclusion of the aforementioned magnetic sensor 10.

[Third Embodiment]

In the following, a magnetic measurement device according to a third embodiment will be explained. Note that the magnetic sensors and the sensor units included in the magnetic measurement device of the third embodiment are applications or modifications of the magnetic sensors or the like of the first and the second embodiments, and items which are not explained in particular are similar to those of the first and the second embodiments.

Figure 9:
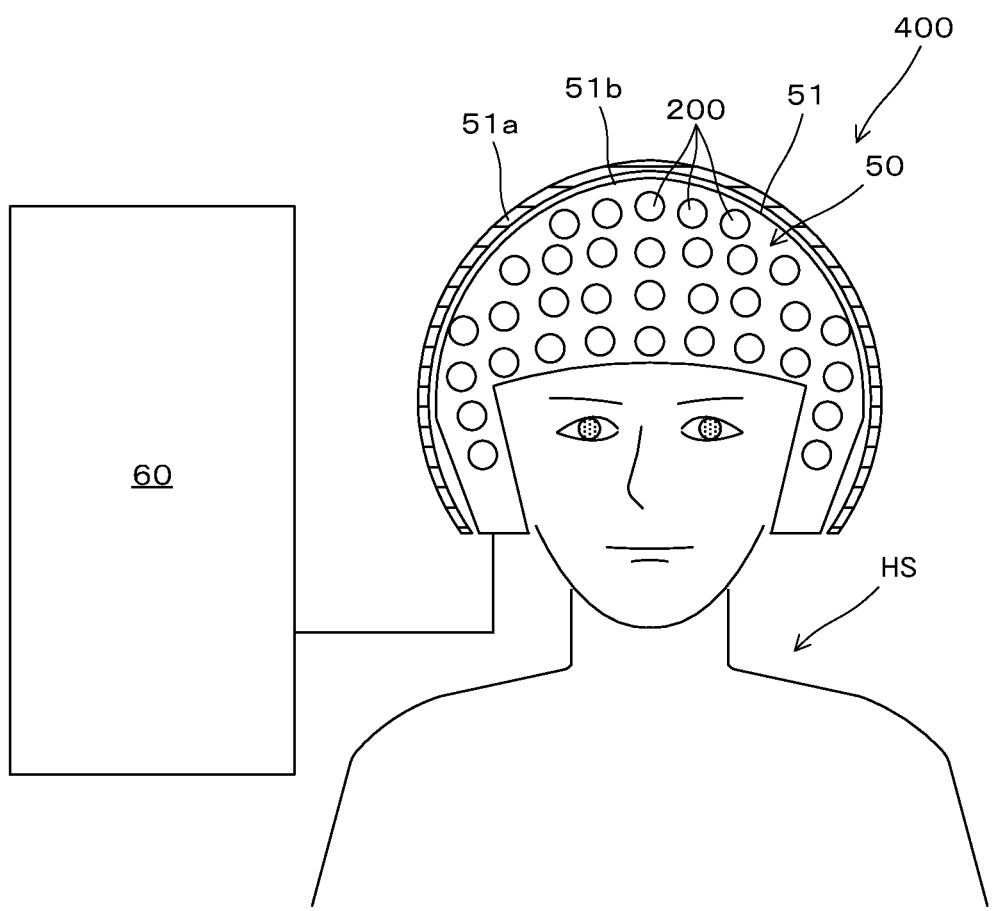
FIG. 9 is a conceptual diagram explaining a magnetic measurement device according to a third embodiment.

As illustrated in FIG. 9, a magnetic measurement device 400 for a biological body includes a biomagnetic field detector 50 and a controller 60.

The biomagnetic field detector 50 is arranged under the influence of a magnetic field from a biological body, and takes out a weak magnetic field from the biological body as a magnetic signal. The biomagnetic field detector 50 has a large number of the sensor units 200 which are similar to those illustrated in FIG. 8 (in other words, a combination of a plurality of the magnetic sensors 10 (see FIG. 1)), and a structure with a large number of these sensor units 200 arranged two-dimensionally. A plurality of the sensor units 200 may be provided on a surface bent so as to conform to the surface of the biological body to be detected. In the example of FIG. 9, the sensor units 200 are built in a helmet-type magnetic shield brace 51 including, for example, a shield block 51a covering the periphery and a main body 51b provided inside the shield block 51a and supporting a number of sensor units 200, and arranged so as to conform to the head of a subject HS. The biomagnetic field detector 50 is attached to the head of the subject HS, and detects the biomagnetism of the subject HS.

The controller 60 performs signal processing on the output of the biomagnetic field detector 50. The controller 60 performs an operation similar to that of the controller 40 of the magnetic detection device 300 explained in the second embodiment.

The aforementioned magnetic measurement device 400 turns out to exhibit an effect of improved biosensitivity and reduced noise by inclusion of the aforementioned magnetic sensor 10. Since the magnetic sensor 10 is minute, two-dimensional or three-dimensional arrangement of the magnetic sensor 10 with a high density allows for improving spatial resolution and a higher precision.

A weak magnetic field from a biological body is said to be about several tens of pT for those induced by the heart, and a little less than 100 pT for those induced by the brain function. The biosensitivity required when detecting the magnetic field will be explained.

Providing the element arrays 10a having a resistance value of 1 kΩ in the bridge circuit VC illustrated in FIG. 1 and applying a voltage of 2 V to the bridge circuit VC results in a voltage of 1 V being applied to each of the element arrays 10a. When, for example, a magnetic field of 1 pT (1,000 times of 1 fT) is applied to each of the element arrays 10a in the above state, a voltage difference of 1 mV occurs on the bridge circuit VC. When, on this occasion, the performance exhibits a noise of about 1 μV, it is possible to detect a brain magnetic field of a little less than 100 pT, for example, with a good SN ratio.

The biosensitivity when signal detection is performed under the aforementioned condition is 1 mV/1 pT in voltage notation, and 0.1%/1 pT in TMR ratio notation (i.e., change rate of resistance value).

Although the magnetic sensor according to the embodiments has been explained above, the magnetic sensor according to the present invention is not limited thereto. For example, the arrangement of the tunnel magnetoresistive elements 20 may be changed as appropriate, in accordance with application. In addition, the magnetization direction of the fixed magnetic layer 21 or the magnetization direction of the free magnetic layer 22 of the tunnel magnetoresistive elements 20 may also be changed as appropriate.

In addition, although the electric circuit 30 is provided with the amplification block 34 and the filter block 35 in the aforementioned embodiments, they need not be provided.

Additionally, in the aforementioned embodiments, the magnetic sensor 10 is configured by combining a plurality of the element arrays 10a with different magnetization directions of the fixed magnetic layer 21 or magnetization directions of the free magnetic layer 22, for example, with the element array 10a, which is an integrated body, being a single unit.

In addition, although the magnetic detection device 300 is formed by the sensor units 200 in the second embodiment, it may be formed by a single magnetic sensor 10.

The invention claimed is:

1. A magnetic sensor comprising:
an element array including a plurality of tunnel magnetoresistive elements respectively having a fixed magnetic layer, a free magnetic layer, and an insulation layer provided between the fixed magnetic layer and the free magnetic layer, the elements respectively for varying the tunnel resistance of the insulation layer by effect of an external magnetic field; and
an electric circuit that applies a voltage to a plurality of the tunnel magnetoresistive elements forming the element array, wherein
the voltage to be applied to each tunnel magnetoresistive element is equal to or higher than 0.5 mV and equal to or lower than 20 mV.

2. The magnetic sensor according to claim 1, wherein the element array is formed by serial connection, parallel connection, or both serial connection and parallel connection of a plurality of the tunnel magnetoresistive elements.

3. The magnetic sensor according to claim 1, wherein the element array includes 20 or more and 10,000 or less of the tunnel magnetoresistive elements connected in series.

4. The magnetic sensor according to claim 1, wherein the resistance value of the element array is equal to or higher than 0.1 kΩ and equal to or lower than 10 kΩ.

5. The magnetic sensor according to claim 1, wherein the resistance value per unit area of the insulation layer of each of the tunnel magnetoresistive elements is equal to or higher than $1 \times 10^3 \Omega/\mu m^2$ and equal to or lower than $1 \times 10^{12} \Omega/\mu m^2$.

6. The magnetic sensor according to claim 1, wherein the insulation layer is made from a material with a coherent tunneling effect.

7. The magnetic sensor according to claim 1, wherein the insulation layer is made from one of: magnesium oxide, spinel, and aluminum oxide.

8. The magnetic sensor according to claim 1, wherein an area of the insulation layer of each of the tunnel magnetoresistive elements is equal to or larger than 1 $\mu m^2$ and equal to or smaller than 1 $mm^2$.

9. The magnetic sensor according to claim 1, wherein the voltage to be applied to the element array is equal to or higher than 0.1 V and equal to or lower than 20 V.

10. The magnetic sensor according to claim 1, wherein the electric circuit has a power source that applies a reference voltage to a pair of serial connections forming a bridge circuit including one or more of the element arrays, a corrector that applies an offset voltage to one of the serial connections forming the bridge circuit, and a feedback block that feeds back, to the corrector, a signal obtained from an output signal between detection terminals of the bridge circuit.

11. The magnetic sensor according to claim 1, wherein the electric circuit includes an amplification block that amplifies an output signal between detection terminals of the bridge circuit, and a filter block having a low-pass filter, a high-pass filter, or both a low-pass filter and a high-pass filter that allow passing of magnetic signals in a predetermined band among the amplification signals from the amplification block.

12. A sensor unit integrated by coupling a plurality of the magnetic sensors according to claim 1 by serial connection, parallel connection, or both serial connection and parallel connection.

13. A magnetic detection device comprising at least one of the magnetic sensors according to claim 1, and a controller that performs signal processing on detection output from the at least one of the magnetic sensors.

14. A magnetic measurement device for a biological body comprising a biomagnetic field detector having a plurality of the magnetic sensors according to claim 1 and provided under influence of a magnetic field from biological body, and a controller that performs signal processing on output of the biomagnetic field detector.

15. The magnetic measurement device according to claim 14 for measuring a magnetic field of equal to or lower than 100 pT.

* * * * *